(12) United States Patent
Itsuji

(10) Patent No.: US 9,360,420 B2
(45) Date of Patent: Jun. 7, 2016

(54) APPARATUS AND METHOD OF MEASURING TERAHERTZ WAVE

(71) Applicant: CANON KABUSHIKI KAISHA, Tokyo (JP)

(72) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/619,529

(22) Filed: Feb. 11, 2015

(65) Prior Publication Data

US 2015/0153274 A1    Jun. 4, 2015

Related U.S. Application Data

(63) Continuation of application No. 13/096,803, filed on Apr. 28, 2011, now Pat. No. 8,981,301.

(30) Foreign Application Priority Data

May 18, 2010   (JP) .................................. 2010-113828
Aug. 5, 2010   (JP) .................................. 2010-175824

(51) Int. Cl.
*G01N 21/3586*   (2014.01)
*G01J 3/42*   (2006.01)

(52) U.S. Cl.
CPC ............... *G01N 21/3586* (2013.01); *G01J 3/42* (2013.01); *G01N 2201/066* (2013.01); *G01N 2201/06113* (2013.01)

(58) Field of Classification Search
CPC .. G01J 5/02; G01N 21/3586; G01N 2201/066
See application file for complete search history.

(56) References Cited

U.S. PATENT DOCUMENTS

2010/0090112 A1*   4/2010   Kawada .................. G01N 21/35
                                                                                250/338.4
2010/0148071 A1*   6/2010   Shioda ............... G01N 21/3581
                                                                                250/341.8

* cited by examiner

*Primary Examiner* — David Porta
*Assistant Examiner* — Faye Boosalis
(74) *Attorney, Agent, or Firm* — Canon USA Inc., IP Division

(57) ABSTRACT

A time-domain waveform of a terahertz wave is measured by a method based on time-domain spectroscopy by using an optical delay unit to adjust an optical path length along which excitation light propagates thereby adjusting a difference between a time at which the excitation light arrives at a generating unit configured to generate the terahertz wave and a time at which the excitation light arrives at a detection unit configured to detect the terahertz wave. The optical delay unit is driven according to a first speed pattern to acquire a first time-domain waveform. The optical delay unit is then driven according to a second speed pattern different from the first speed pattern to acquire a second time-domain waveform. The first time-domain waveform and the second time-domain waveform are averaged.

8 Claims, 8 Drawing Sheets

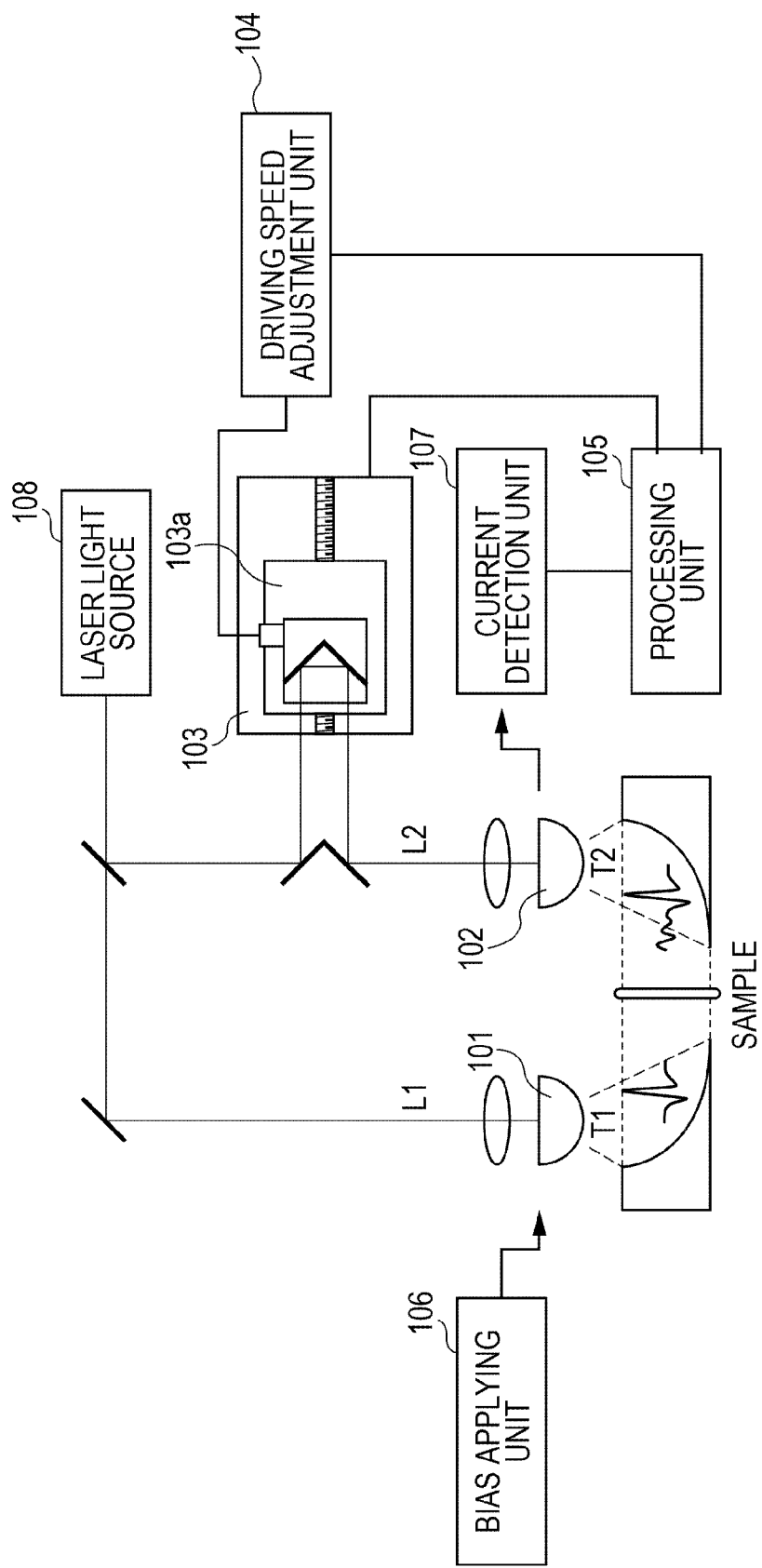

Vmin = Vmax · Vave/(2Vmax − Vave)

APPARATUS AND METHOD OF MEASURING TERAHERTZ WAVE

CROSS-REFERENCE TO RELATED APPLICATIONS

This application is a Continuation of co-pending U.S. patent application Ser. No. 13/096,803, filed Apr. 28, 2011, which claims foreign priority benefit of Japanese Patent Application No. 2010-113828 filed May 18, 2010 and Japanese Patent Application No. 2010-175824 filed Aug. 5, 2010. The above-named applications are hereby incorporated by reference herein in their entirety.

BACKGROUND OF THE INVENTION

1. Field of the Invention

The present invention relates to an apparatus and a method of measuring a terahertz wave, and more particularly, to an apparatus and a method of measuring a terahertz wave in a time domain. Hereinafter, such as an apparatus will be also referred to as a THz TDS (Time Domain Spectroscopy) apparatus.

2. Description of the Related Art

A terahertz wave is an electromagnetic wave with a frequency in an arbitrary frequency band within a range from 0.03 THz to 30 THz. This frequency range includes many frequencies or bands of frequency at which characteristic absorption occurs due to structures or states of substances such as biological molecules. This feature is usable to non-destructively analyze or identify a substance, and associated techniques have been developed. One example of a predicted application is a safety imaging technique usable instead of an X-ray imaging technique. Another example of a predicted application is a high-speed communication technique.

In the time domain, terahertz waves generally have a form of a pulse with a width of sub-pico seconds. It is generally difficult to acquire such a pulse in real time because of the slow response that current electronics have with respect to the speed of THz waves. To overcome such a difficultly, a conventional THz-TDS apparatus employs a sampling measurement technique using ultrashort pulse light with a pulse width on the order of femto seconds. The sampling of the terahertz wave is achieved by adjusting a difference between a time at which excitation light arrives at a generating unit that generates the terahertz wave and a time at which the excitation light arrives at a detection unit that detects the terahertz wave. For example the time difference can be provided by disposing a stage having a folded optical system (also referred to as an optical delay unit in the present description) in a propagation path of the excitation light and adjusting the total round-trip length of the excitation light in the folded optical system (see, for example, Japanese Patent Laid-Open No. 2008-20268). In many cases, the generating unit and/or the detection unit is realized using a photoconductive device including an antenna electrode pattern having small gaps formed on a semiconductor film.

In the THz-TDS apparatus, an increase in the measurement sensitivity can result in an increase in effects of a vibration of the stage of the optical delay unit. More specifically, the vibration of the stage used in the optical delay unit causes the optical axis of the excitation light to swing. This causes a change in the amount of light per unit area that strikes the small gaps of the photoconductive device. Thus, a vibration component is superimposed on the time-domain waveform of the terahertz wave reproduced by the apparatus. If such a time-domain waveform is subjected to a Fourier transform, then, as shown in FIG. 6, a resultant spectrum 623 of the terahertz wave detected by the detection unit includes a spurious component 624 due to the vibration of the optical delay unit. For example, when a vibration component of several hundred Hz is superimposed on a time-domain waveform of a terahertz wave, a spurious spectrum appears typically at 4 THz to 6 THz although the spurious spectrum varies depending on the configuration of the measurement system and/or the driving condition of the optical delay unit. Such a spurious spectrum can limit a measurement bandwidth of the measurement apparatus and can cause a reduction in analysis performance thereof. As can be seen from the above description, in the terahertz wave measurement apparatus, there is a need for suppression of effects of vibrations of an optical delay unit.

SUMMARY OF THE INVENTION

According to an aspect, the present invention provides a method of measuring a time-domain waveform of a terahertz wave based on time-domain spectroscopy by using an optical delay unit to adjust an optical path length along which excitation light propagates thereby adjusting a difference between a time at which the excitation light arrives at a generating unit configured to generate the terahertz wave and a time at which the excitation light arrives at a detection unit configured to detect the terahertz wave, the method includes driving the optical delay unit according to a first speed pattern to acquire a first time-domain waveform, driving the optical delay unit according to a second speed pattern different from the first speed pattern to acquire a second time-domain waveform, and averaging the first time-domain waveform and the second time-domain waveform.

In the method according to one aspect of the invention, the speed pattern used to drive the optical delay unit is changed for each measurement of the time-domain waveform, and measurement results are averaged. Changing the speed pattern results in a change in sampling time intervals at which data is acquired to reproduce the time-domain waveform of the terahertz wave. The time-domain waveform of the terahertz wave reproduced does not depend on the sampling time intervals. However, the change in the sampling time interval causes a change in shape of a signal component having substantially no relation with the terahertz wave. This property makes it possible to suppress the signal components having the small relation with the terahertz wave by averaging data obtained for various speed patterns. Thus, it becomes possible to suppress a spurious spectrum superimposed on a frequency spectrum and it becomes possible to increase a measurement bandwidth.

Further aspects of the present invention will become apparent to persons having ordinary skill in the art from the following description of exemplary embodiments with reference to the attached drawings.

BRIEF DESCRIPTION OF THE DRAWINGS

FIG. 1 is a diagram illustrating an example of a configuration of a measurement apparatus according to an embodiment of the invention.

DESCRIPTION OF THE EMBODIMENTS

Figure 2A:
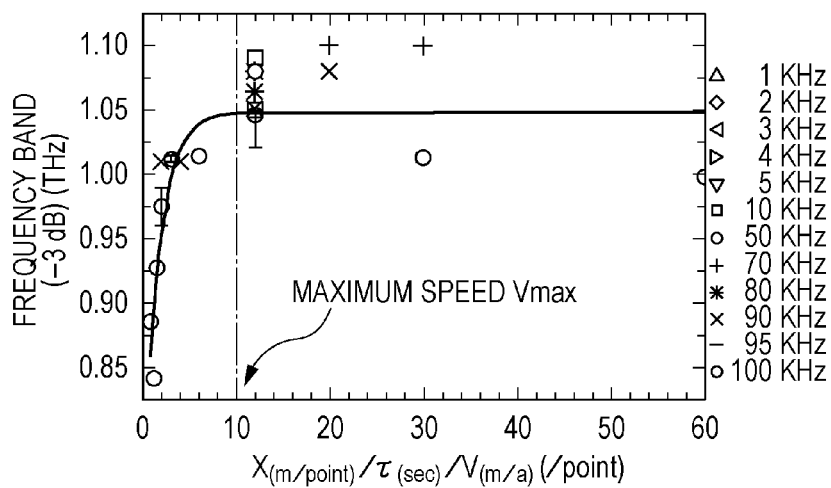
FIG. 2A is a graph illustrating a maximum speed Vmax included in a speed pattern.

In an apparatus and a method of acquiring a time-domain waveform of a terahertz wave using time-domain spectroscopy according to an aspect of the present invention, a plurality of time-domain waveforms are acquired by driving an optical delay unit according to a plurality of different speed patterns, and a final time-domain waveform is acquired by averaging the plurality of time-domain waveforms. A basic configuration and a spirit of the apparatus and the method of acquiring the time-domain waveform of the terahertz wave using the time-domain spectroscopy according to an aspect of the invention have been described above.

Next, specific embodiments of the invention are described below with reference to the accompanying drawings. FIG. 1 is a diagram illustrating an example of a configuration of a terahertz wave measurement apparatus according to an embodiment of the invention. As shown in FIG. 1, the apparatus includes a generating unit 101, a detection unit 102, an optical delay unit 103 including a moving part 103a, a driving speed adjustment unit 104, a processing unit 105, a bias applying unit 106, a current detection unit 107, and a laser light source 108.

The generating unit 101 is a device that generates a terahertz wave. In the generating unit 101, the terahertz wave may be generated by a method using an instantaneous current or a method using interband transition of carriers. In the method using the instantaneous current, the terahertz wave may be generated using a technique of illuminating a surface of a semiconductor or an organic crystal with excitation light. In this technique, the illuminating of the excitation light may be performed while applying an electric field to a device (photoconductive device) having a metal antenna pattern formed on a thin semiconductor film. Alternatively, a positive-intrinsic-negative (PIN) diode may be used. On the other hand, in the method using the interband transition of carries in the gain structure, a semiconductor quantum well structure may be used. It is expected that persons having ordinary skill in the art would be familiar with these and other conventional structures useful for terahertz-wave generation.

The detection unit 102 is a unit that detects the electric field intensity of the terahertz wave. In the detection unit 102, the electric field intensity of the terahertz wave may be detected by detecting a current that occurs in response to a change in photoconductivity caused by illumination of the excitation light. In this technique, the current may be detected using a photoconductive device of the type described above. An alternative method is to detect an electric field using an electrooptical effect. A further alternative method is to detect a magnetic field using a magnetooptical effect. A specific example of the method of detecting the electric field using the electrooptical effect is to use a polarizing beam splitter (polarizer) and an electrooptical crystal. A specific example of the method of detecting the magnetic field using the magenetooptical effect is to use a polarizing beam splitter (polarizer) and a magnetooptical crystal. In the following description, by way of example, the generating unit 101 and the detection unit 102 are each implemented using a photoconductive device.

In the present embodiment, the laser light source 108 is a coherent light source that outputs ultrashort (generally pico or femtosecond) pulses of light. The above-described generating unit 101 and the detection unit 102 are configured to operate by irradiating a thin semiconductor film with the ultrashort pulse of laser light to excite carries in the thin semiconductor film. In the present description, in view of the above, the ultrashort pulse laser light is also referred to as excitation light. As shown in FIG. 1, the excitation light emitted from the light source 108 is split into two optical paths L1 and L2. In the present embodiment, the excitation light passing through the optical path L1 illuminates the generating unit 101. The excitation light passing through the optical path L2 illuminates the detection unit 102 via the optical delay unit 103 described later.

In many cases, the time-domain waveform of a terahertz wave is in a form of a pulse with a width of picoseconds or less, and thus it is difficult to acquire the waveform of the terahertz wave in real time. For this reason, the time-domain waveform of the terahertz wave is acquired via a sampling measurement process using the excitation light. The optical delay unit 103 is configured to adjust the delay time between a time at which the terahertz wave is generated by the generating unit 101 and a time at which the terahertz wave is detected by the detection unit 102 to adjust sampling points at which data is acquired to produce the time-domain waveform of the terahertz wave. More specifically, the time for the excitation light to arrive at the detection unit 102 is delayed with respect to the time for the excitation light to arrive at the generating unit 101. The difference in arrival time of the excitation light between the generating unit 101 and the detection unit 102 may be controlled by directly adjusting the length of the optical propagation path of the excitation light or by adjusting the effective length of the optical path. A specific method of the direct adjustment of the optical path length is to provide a folded optical system in which excitation light is reflected back and move this optical system in the same direction as the folded direction of the optical path by using the moving part 103. A specific method of adjusting the effective length of the optical path is to change a time constant (refractive index) in the optical path along which the excitation light propagates. In the example shown in FIG. 1, a one-stage folded optical system and a linear motion stage serving as the moving part 103a are used. In this example, the operation of the moving part 103a is controlled by the driving speed adjustment unit 104 that will be described in further detail later. The optical path length L2 from the laser light source 108 to the detection unit 102 is changed by changing the position of the folded optical system by using the moving part 103a. The change in the optical path length is controlled such that the difference in optical path length L2−L1 causes a particular time difference between a time at which the excitation light reaches the generating unit 101 and a time at which the excitation light reaches the detection unit 102. If the driving speed of the moving part 103a is high, the time-domain waveform of the terahertz wave can be acquired in a short time.

The bias applying unit 106 is a unit that provides a bias to drive the generating unit 101. In a case where a photoconductive device is used as the generating unit 101, a voltage is applied to a metal electrode including an antenna pattern. In particular, when the current detection unit 107 (described later) includes a lockin detection system, the voltage supplied by the bias applying unit 106 is modulated by a frequency equal to that of a reference signal in the lockin detection system. In the lockin detection, instead of modulating the bias supplied by the bias applying unit 106, the modulation may be achieved by modulating the excitation light using an optical chopper. In the latter method, the bias applying unit 106 applies a DC bias directly to the photoconductive device.

The current detection unit 107 may be a circuit that converts a current signal into a voltage signal with a measurable level. When a photoconductive device is used as the detection unit 102, the current detection unit 107 converts a current signal output from the detection unit 102 into a voltage signal. The conversion ratio of the current signal to the voltage signal is referred to as a current-to-voltage conversion ratio. The current-to-voltage conversion ratio is selected within a range that allows the current detection unit 107 to convert the current signal input thereto to the voltage signal without causing the output of the current detection unit 107 to exceed a rated value specified for the circuit. To increase the signal-to-noise ratio of the measurement apparatus, the current-to-voltage conversion ratio may be set to be as large as possible. As described above, when the signal output from the detection unit 102 is weak, the current detection unit 107 may include a lockin detection system. More specifically, the lockin detection system is disposed at a final stage of a circuit that performs the current-to-voltage conversion. In the case where the current detection unit 107 includes the lockin detection system, the circuit that performs the current-to-voltage conversion is set such that the amplitude of the signal output therefrom does not exceed the input rating of the lockin detection system. Note that the current detection unit 107 may be replaced with another unit configured to provide, based on the signal output from the detection unit 102, a signal that can be easily processed by the processing unit 105.

The processing unit 105 is a unit that provides measurement data by producing the time-domain waveform of the terahertz wave. The time-domain waveform is produced based on the amount of change in the optical path length of the optical delay unit 103 and the output of the current detection unit 107. More specifically, the time-domain waveform is produced by plotting the output of the current detection unit 107 in steps of predetermined amounts of change in the optical path length. The predetermined amount of change in the optical path length corresponds to a time interval t of the measurement data. The measurement data is obtained in the form of a series of intensity data plotted at time intervals t, and the obtained measurement data is stored. To improve the signal-to-noise ratio of the measurement apparatus, the linear motion stage of the optical delay unit 103 may be stopped at each measurement point (or the speed is reduced to a level that can be regarded as being substantially at rest), and outputs provided by the current detection unit 107 are averaged to obtain a final time-domain waveform. This technique is referred to as a step-and-scan method. An alternative technique is to acquire the time-domain waveform a plurality of times while driving the linear motion stage of the optical delay unit 103 at a high speed. The acquired time-domain waveforms are averaged by the processing unit 105 for respective elements of the sequence of measured intensity data. This technique is referred to as a rapid scan method. As described above, the time-domain waveform is acquired a plurality of times to obtain a plurality of sets of data of the time-domain waveform, and the plurality of sets of data are averaged by the processing unit 105 to increase the signal-to-noise ratio of the signal.

To output spectrum data in the frequency domain, the processing unit 105 refers to the measurement data and performs a Fourier transform on the time-domain waveform of the terahertz wave to acquire the spectrum data. When the THz-TDS apparatus is used as an analysis apparatus, a sample (specimen) is irradiated with a terahertz wave and a change in time-domain waveform of the terahertz wave caused by the irradiation is determined. More specifically, the specimen is irradiated with the terahertz wave generated by the generating unit 101, and the terahertz wave passing through the specimen or the terahertz wave reflected from the specimen is detected by the detection unit 102. Based on the obtained time-domain waveform, information on the specimen is acquired. The processing unit 105 may acquire an image of the sample by monitoring a relative position between the sample and the terahertz wave irradiating the sample. With the configuration described above, the THz-TDS apparatus monitors a change in optical path length of excitation light provided by the optical delay unit 103 and a corresponding change in output of the current detection unit 107, and the THz-TDS apparatus produces a time-domain waveform of the terahertz wave irradiating the detection unit 102.

A typical known configuration of the THz-TDS apparatus has been described above. In the present embodiment, in addition to the configuration described above, the apparatus further includes the driving speed adjustment unit 104. The driving speed adjustment unit 104 makes it possible to acquire the time-domain waveform of a terahertz wave by a unique method according to the present embodiment of the invention. The driving speed adjustment unit 104 is a unit that manages and adjusts the speed of the moving part 103a of the optical delay unit 103. Note that the speed of the moving part 103a is managed for each time-domain waveform measured. More specifically, the moving part 103a is driven at a particular speed that is changed for each measurement of the time-domain waveform. The speed of the moving part 103a may be changed even during a process of measuring a single time-domain waveform. In the present description, a mode of changing the speed is defined by a speed pattern. The driving speed adjustment unit 104 manages the speed pattern and provides the managed speed pattern.

Figure 5A:
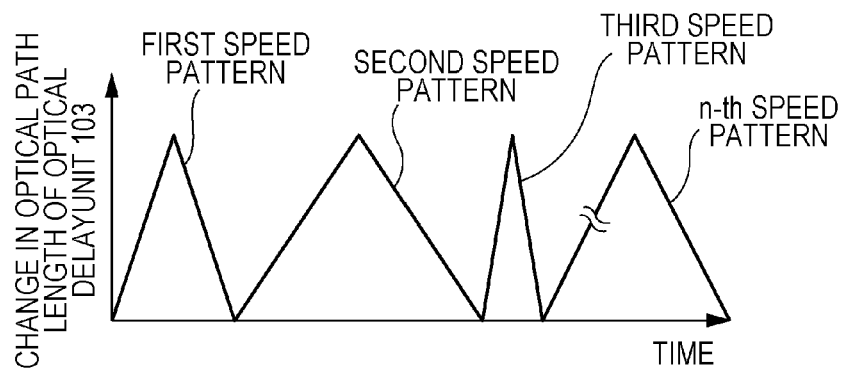
FIG. 5A is a graph provided for explaining a measurement apparatus, a method, and a plurality of speed patterns according to an embodiment of the present invention.
Figure 5B:
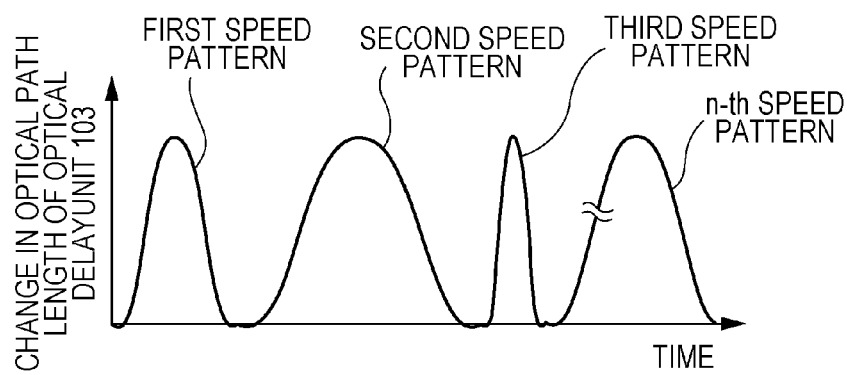
FIG. 5B is a graph provided for explaining a measurement apparatus, a method, and a plurality of speed patterns according to an embodiment of the present invention.
Figure 5C:
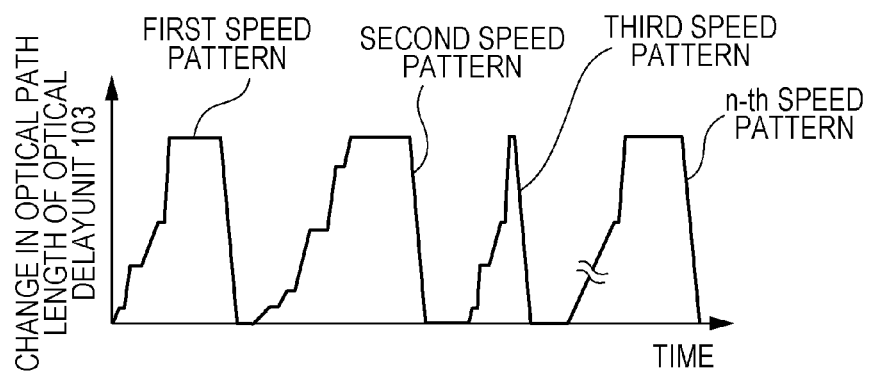
FIG. 5C is a graph provided for explaining a measurement apparatus, a method, and a plurality of speed patterns according to an embodiment of the present invention.
Figure 6:
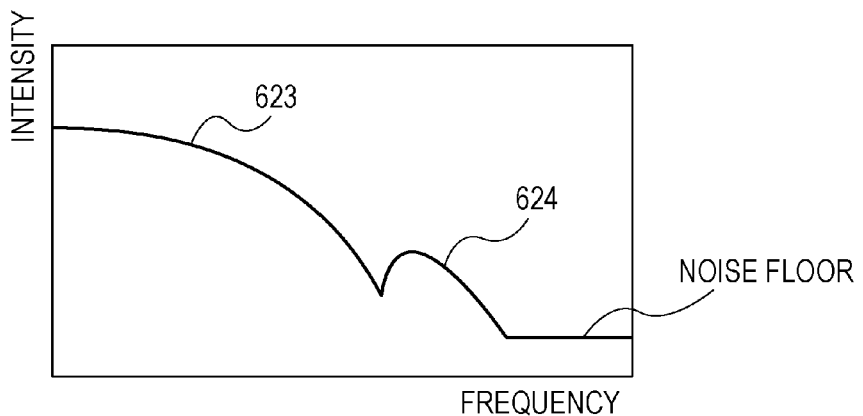
FIG. 6 is a graph illustrating a problem to be solved by an embodiment of the present invention.

FIGS. 5A to 5C illustrate examples of speed patterns managed by the driving speed adjustment unit 104. More specifically, FIGS. 5A to 5C illustrate examples of changes in optical path length of the optical delay unit 103 as a function of an elapsed time. That is, by continuously detecting the change in optical path length with the elapsed time, it is possible to determine and control the driving speed of the moving part 103a of the optical delay unit 103. As can be seen, the change in optical path length is folded at a particular value, because the moving part 103a moves back and forth. As shown in FIGS. 5A to 5C, a different speed pattern is defined for each round trip of the movement of the moving part 103a. The time-domain waveform of a terahertz wave is produced for each round trip of the moving part 103a. And, since each round trip of the moving part 103a is performed at a different speed pattern, a time-domain waveform is produced for each speed pattern by the processing unit 105. In each of the examples shown in FIGS. 5A to 5C, there are n speed patterns defined, and thus the time-domain waveform of the terahertz wave is produced n times.

FIG. 5A illustrates an example in which the speed pattern is managed for each measurement of the time-domain waveform. In this example, each speed pattern changes at a constant speed in each measurement of the time-domain waveform of the terahertz wave. Specifically, in the example of FIG. 5A, when the moving part 103a moves under the first speed pattern, the optical path length changes constantly at a first speed; when the moving part 103a moves under the second speed pattern, the optical path length changes constantly at a second speed different from the first speed. The same applies for the third to n-th speed patterns. FIG. 5B illustrates an example in which the driving of the moving part 103a is performed at a varying speed during each measurement of the time-domain waveform. That is, in this example, each speed pattern changes at a non-constant speed in each measurement of the time-domain waveform of the terahertz wave. Specifically, in the example of FIG. 5b, when the moving part 103a moves under the first speed pattern, the optical path length changes at a varying first speed; and when the moving part 103a moves under the second speed pattern, the optical path length changes at a varying second speed different from the varying first speed. The same applies for the third to n-th speed patterns. FIG. 5C illustrates an example in which a waiting period with a fixed length (during which the optical path length is maintained unchanged, i.e., the speed of the moving part 103a is zero) is provided after a measurement point is reached in each speed pattern, and the driving speed is changed again after the end of the waiting period. In the example shown in FIG. 5C, the back-and-forth movement of the moving part 103a is performed such that the speed pattern in a backward direction is different from that in a forward direction. Note that the speed pattern may be set to be different between the forward and backward directions also in the previous examples described above. Note that in conventional THz-TDS apparatuses, the same speed pattern is used for all measurement cycles. In contrast, in the present embodiment of the invention, the speed pattern is different for each measurement of the time-domain waveform of the terahertz wave.

Figure 2B:
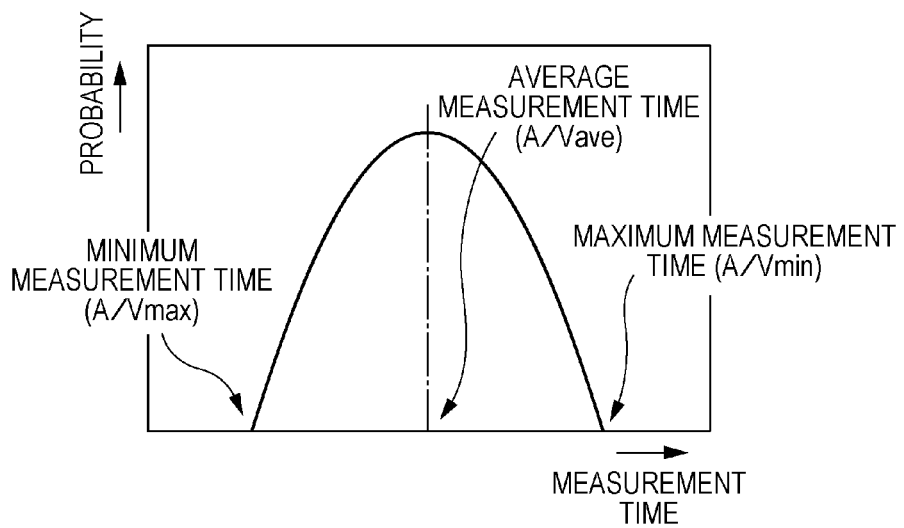
FIG. 2B is a graph illustrating a minimum speed Vmin included in a speed pattern.

Referring to FIGS. 2A and 2B, an explanation is given below as to a limitation on the speed in the speed patterns. FIG. 2A illustrates a maximum speed Vmax in a speed pattern. More specifically, FIG. 2A illustrates a band of a frequency spectrum of a terahertz wave as a function of a speed of change in the length of the optical path of the excitation light adjusted by the optical delay unit 103.

In FIG. 2A, X included in a variable in a horizontal axis indicates a change in optical path length (m/point) per a predetermined time interval (denoted as a point in FIG. 2A) at which a time-domain waveform of a terahertz wave is sampled to acquire measurement data of the time-domain waveform. The change in optical path length divided by the speed of light equals to the predetermined time interval. $\tau$ is a time constant of the THz-TDS apparatus. For example, in a case where the apparatus is configured to perform a lockin detection using a lockin amplifier, $\tau$ generally has a value corresponding to a time constant of the lockin amplifier.

V denotes the speed of the change in the optical path length adjusted by the optical delay unit 103. Thus, the variable $X/\tau/V$ (X divided by $\tau$ and further divided by V) in the horizontal axis indicates a value normalized by $\tau$ in terms of a time X/V needed to achieve a particular change in the optical path length. The speed V of the change in optical path length decreases with increasing value in the horizontal axis. A vertical axis indicates a frequency band defined by a frequency at which the electric field intensity of the frequency spectrum of the acquired terahertz wave has a negative 3 decibel (−3 dB) value with respect to the highest value. In FIG. 2A, data is plotted while changing the modulation frequency of the bias applying unit 106 from 1 KHz to 100 KHz. A solid line indicates an approximate curve determined so as to fit the plotted data. In FIG. 2A, from a change in gradient of a tangent to the approximate curve, it can be seen that an inflection point occurs at approximately $X/\tau/V=5$. When $X/\tau/V$ is in a range equal to or greater than 10, the approximate curve with a gradient of 0 fits well the plotted data. When $X/\tau/V$ is smaller than 5, the speed of the change in the optical path length is likely to become excessively large with respect to the time constant $\tau$ of the apparatus. That is, the speed of the change in the optical path length can become too fast, that the lockin amplifier can no longer detect and control change in the optical path. This can lead to an increase in tendency to have noise and an increase in probability that it becomes difficult to accurately capture the time-domain waveform of the terahertz wave.

In view of the above, preferably, the maximum speed Vmax in the speed pattern is set such that X/$\tau$/Vmax is equal to or greater than 5, and more preferably equal to or greater than 10. By limiting the maximum speed of the change in the optical path length in the above-described manner such that the measurement apparatus can respond to the change during the process of acquiring the data, it becomes possible to suppress the negative effect of the time constant of the measurement apparatus on the time-domain waveform of the terahertz wave and thus it becomes possible to stably acquire the time-domain waveform of the terahertz wave. Note that, as can be seen from FIG. 2A, the data does not significantly depend on the modulation frequency.

Referring to FIG. 2B, a minimum speed Vmin in each speed pattern is discussed below. In FIG. 2B, a horizontal axis indicates a time needed to acquire a time-domain waveform, and a vertical axis indicates a probability of occurrence of such a time. In the present embodiment, an average speed Vave is determined and a total measurement time needed for the THz-TDS apparatus to perform the measurement is predicted based on the average speed Vave. The average speed Vave is determined by an operator by dividing the optical path length A needed to acquire the time-domain waveform by the average time needed to acquire one time-domain waveform. The speed included in the speed pattern has a distribution around the average speed Vave.

In the example shown in FIG. 2B, the measurement time performed using the speed included in the speed pattern has a normal distribution around the time (A/Vave) needed for the measurement apparatus to adjust the optical path length A with the average speed Vave. That is, the measurement time has a normal distribution in a range from a minimum measurement time (A/Vmax) needed when the driving is performed at a maximum speed Vmax to a maximum measurement time (A/Vmin) needed when the driving is performed at a minimum speed Vmin. Note that the minimum speed Vmin is defined as Vmax·Vave/(2Vmax−Vave). In the case of the speed pattern including a waiting period such as that shown in FIG. 5C, the minimum speed Vmin is calculated for a period excluding the waiting period, i.e., the minimum speed is defined for the period in which the optical path length changes.

Vmax and Vmin may be set such that the time difference between the average measurement time and the minimum measurement time and the time difference between the average measurement time and the maximum measurement time are as large as allowed. In other words, an adjustment is made to maximize the difference between Vave and Vmax and the difference between Vave and Vmin. The adjustment of the Vave, Vmax, and Vmin in the above-described manner makes it possible to provide a wide variety of speed patterns usable, which makes it possible to more effectively suppress spurious spectra.

In the apparatus and the method according to the present embodiment of the invention, Vmax and Vmin are determined in the above-described manner to prevent an occurrence of a state in which extra measurement time is spent in acquisition of the time-domain waveform. That is, by setting the driving speed included in the speed pattern defining the change in the optical path length such that the driving speed has a distribution around the average speed determined by an operator based on the maximum speed, it becomes possible to predict an approximate time needed to acquire a time-domain waveform of a terahertz wave, which makes it possible to perform a measurement in an efficient manner. Note that the time does not need to have a normal distribution, but the time may have other distributions such as a rectangular-shape distribution, and the speed pattern may be set such that the measurement time has a distribution around the average measurement time. The speed distributions in speed patterns may be adjusted such that a first speed pattern and a second speed pattern are different in shape but each speed pattern has a similar distribution. In this case, even when a measurement is terminated before the measurement is performed the predetermined number of times, the same speed distribution is obtained. Alternatively, the speed may have a particular distribution such as that shown in FIG. 2B as a whole from the first speed pattern to the n-th speed pattern.

Indeed, a plurality of speed patterns may be determined in advance and may be stored in the driving speed adjustment unit 104. Alternatively, speed patterns may be produced as required based on the average speed defined by the operator and/or the maximum speed and the minimum speed. That is, after Vave, Vmax, and Vmin have been determined, the driving speed adjustment unit 104 may produce a plurality of speed patterns according to a particular condition. For example, the driving speed adjustment unit 104 may produce speed patterns such that each speed pattern is divided into one or more time slots represented in time domain. And, a speed changing mode may be selected randomly or according to a predetermined selection rule from a predetermined group of values corresponding to a plurality of speed changing modes. Each selected speed changing mode can then be assigned to each time slot thereby producing the plurality of speed patterns. In this manner, a predetermined speed pattern can be applied at each time slot to manage and adjust the speed of the moving part 103a. In the producing of the plurality of speed patterns, data shown in FIGS. 2A and 2B may be referred to. The group of speed changing modes may include, for example, a constant speed mode (a linearly changing mode), a sinusoidally changing mode, a quadratically changing mode, etc. The group of speed changing modes may be stored in a non-illustrated storage area of the driving speed adjustment unit 104.

Next, referring FIG. 1, FIGS. 3A to 3D, FIG. 4, and other figures as required, the measurement apparatus, the method, and the operation of the measurement apparatus according to embodiments of the present invention are described below. FIGS. 3A to 3D illustrate signals input to and output from the processing unit 105 in the apparatus in operation steps according to the method disclosed herein. FIG. 4 illustrates a flow of the operation performed by the measurement apparatus according to the method. In FIG. 4, when the terahertz wave measurement apparatus starts a measurement, the driving speed adjustment unit 104 sets a first speed pattern according to which to control the optical delay unit 103 (step S401). The optical delay unit 103 adjusts the optical path length of excitation light according to the first speed pattern. In the following explanation, it is assumed by way of example that the first speed pattern is set such that the optical path length changes at a constant driving speed V as shown in FIG. 5A. If the driving speed V is high, the optical path length changes quickly. On the other hand, if the driving speed V is low, the optical path length changes slowly. Specifically, as illustrated in FIG. 5A, the first speed pattern has a steeper slope than the second speed pattern. This means that the optical path length would constantly change faster when driven according to the first speed pattern than it would when driven according to the second speed patter. The processing unit 105 monitors a change in the optical path length. Each time a predetermined amount of change in optical path length is observed, the processing unit 105 acquires a value of a current detected by the current detection unit 107. This process is referred to as sampling.

Figure 3A:
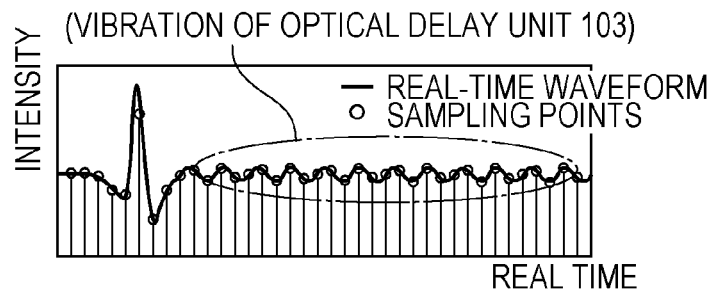
FIG. 3A is a graph provided for explaining a measurement apparatus, a method, and a process according to an embodiment of the present invention.
Figure 3B:
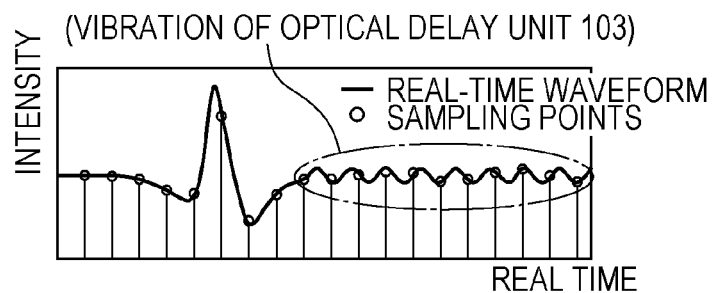
FIG. 3B is a graph provided for explaining a measurement apparatus, a method, and a process according to an embodiment of the present invention.
Figure 3C:
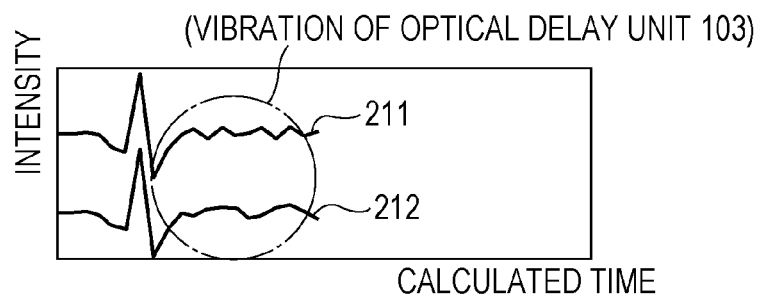
FIG. 3C is a graph provided for explaining a measurement apparatus, a method, and a process according to an embodiment of the present invention.
Figure 4:
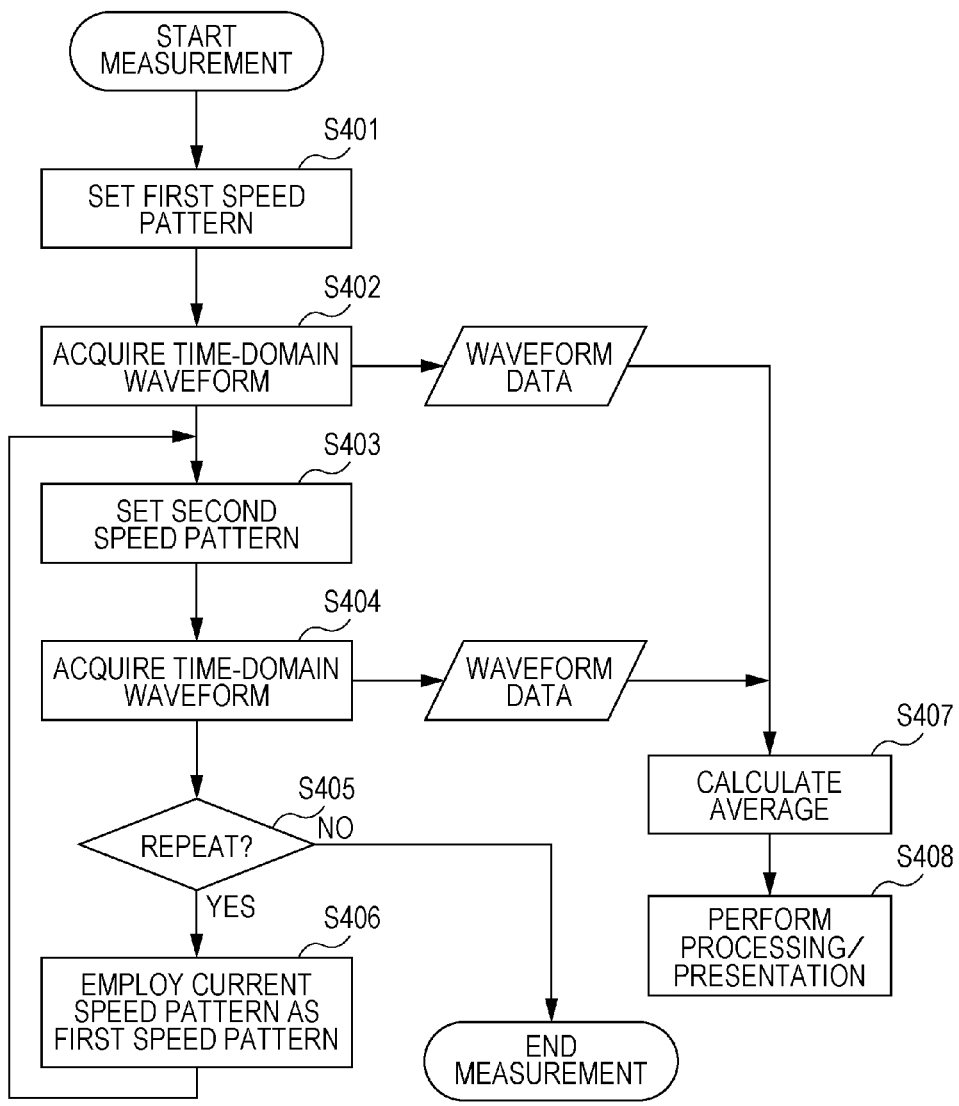
FIG. 4 is a flow chart associated with a measurement apparatus, a method, and an operation according to an embodiment of the present invention.

FIG. 3A illustrates a real-time waveform output from the current detection unit 107 (for example, a waveform obtained when the output of the current detection unit 107 is measured by an oscilloscope) for various sampling points. The real-time waveform is obtained in the process of changing the optical path length. More specifically, the values of the real-time waveform along the time axis are calculated from the amount of change in optical path length and the speed at which the optical path length is changed. For example, a peak of a terahertz wave pulse occurs when the optical path length changes by a particular fixed amount. Similarly, there is a fixed relationship between each point in the time-domain waveform of the terahertz wave and the amount of change in optical path length. However, the time needed to reach a particular point of the time-domain waveform of the terahertz wave depends on the speed at which the optical path length is changed. Thus an apparent contraction occurs for the real-time waveform of the terahertz wave when the optical path length is changed at high speed. Conversely, when the optical path length is changed at a low speed, the real-time waveform of the terahertz wave expands compared with the example described above. That is, signal components of a terahertz wave (T1 or T2) propagating in space can change such that the real-time waveform represented in time-domain expands or contracts depending on the speed pattern used. In view of the above, the processing unit 105 acquires a value detected by the current detection unit 107 each time a predetermined fixed amount of change occurs in the optical path length. The processing unit 105 determines the time corresponding to the predetermined amount of change in optical path length (the time can be calculated by dividing the change in optical path length by the speed of light) and plots the data to obtain a first time-domain waveform 211 as shown in FIG. 3C (step S402).

Note that the effect of the speed pattern is suppressed in the waveform obtained in this manner.

After the time-domain waveform is obtained using the first speed pattern, the driving speed adjustment unit 104 sets a second speed pattern, different from the first speed pattern, for use in controlling the optical delay unit 103 (step S403). Herein it is assumed by way of example that the second speed pattern is set such that the optical path length changes at a constant driving speed V/2 where V is the driving speed used in the first speed pattern. Use of this second speed pattern with the driving speed one-half that of the first speed pattern causes the real-time signal output from the current detection unit 107 to expand in the real time axis by a factor of two compared with the signal obtained when the first speed pattern is used, as shown in FIG. 3B. As described above, the processing unit 105 acquires the value detected by the current detection unit 107 each time the predetermined fixed amount of change occurs in the optical path length. Therefore, the time needed to achieve the same predetermined amount of change is twice longer than in the above case (FIG. 3A), and thus the sampling period expands by a factor of two in the real time axis. A waveform of a signal component caused by an operation of the measurement apparatus, such as a fixed vibration component caused by the driving of the optical delay unit 103, is insensitive to a change in speed pattern. As can be seen from FIGS. 3A and 3B, signal components associated with terahertz waves (T1 and T2) propagating in space change in shape in response to a change in speed pattern, but only slight changes occur in the fixed signal components (such as the vibration of the optical delay unit 103) that are produced by the operation of the measurement apparatus and are superimposed on the main signal components. For the second speed pattern, the processing unit 105 acquires the value detected by the current detection unit 107 each time the predetermined fixed amount of change occurs in the optical path length. The processing unit 105 determines the time corresponding to the predetermined amount of change in optical path length and plots the data to obtain a second time-domain waveform 212 as shown in FIG. 3C (step S404).

As can be seen from comparison between the obtained first time-domain waveform 211 and second time-domain waveform 212, components associated with terahertz waves propagating in space have the same shape because there is a fixed relationship between the point in the time-domain waveform of the terahertz wave and the amount of change in the optical path length. On the other hand, for the components of the signal (such as the vibration waveform of the optical delay unit 103 shown in detail in the circle of FIG. 3C) that are fixed in the time domain regardless of the speed pattern, there is substantially no correlation with the amount of change in the optical path length. Therefore, when the processing unit 105 changes the sampling interval and acquires data at different points, the fixed signal has different time-domain waveforms depending on speed patterns as shown in FIG. 3C. That is, the time-domain waveform produced by the processing unit 105 has a property that the signal components associated with the terahertz wave propagating in space are the same in waveform regardless of the speed pattern, but the signal components having less correlation with the terahertz wave vary in waveform depending on the speed pattern.

After the acquisition of the second time-domain waveform is completed, the measurement apparatus determines whether to continue the measurement of the time-domain waveform (step S405). For example, when the measurement has been performed a predetermined number of times, the measurement of the time-domain waveform is ended.

Alternatively, the measurement may be ended when it is determined in a following processing step that a predetermined ending condition (for example, in terms of a particular characteristic such as a signal-to-noise ratio) is satisfied. In a case where it is determined that the measurement is to be continued, the second speed pattern used in the second measurement of the time-domain waveform is redefined as the first speed pattern (step S406). The driving speed adjustment unit 104 then sets a second speed pattern, different from the redefined first speed pattern, for use in controlling the optical delay unit 103 (step S403), and measures the time-domain waveform using the second speed pattern.

As described above, the processing unit 105 reproduces data from each measured time-domain waveform by converting the amount of change in optical path length into the corresponding time by the calculation. The processing unit 105 averages the data into a single time-domain waveform (step S407). The averaging may be performed by adding a plurality of sets of data, for example, corresponding to a predetermined time slot of the time-domain waveform for each value in change in the optical path length and determining the mathematical average. Alternatively, data may be preprocessed and the average may be determined for the preprocessed data. An example of preprocessing is to correct baselines of measured time-domain waveforms. Another example is to perform fast-Fourier-transform (FFT) filtering to suppress a signal in a particular frequency range. A further example is to perform a wavelet transform to suppress system noise or a varying component in a measurement environment. A still another example is to enhance data in a particular time range (time slot in time domain) by using a time window. In addition to determining a mathematical average of the first to n-th time-domain waveforms, a weighted average can be calculated, based on a predetermined weighting function of value thereof. For example, a peak of the terahertz wave that occurs substantially at the same point in time in the first to n-th waveforms can be assigned a weight value of 90% or higher, while peaks that do not occur at the substantially the same point in time in the first to n-th waveforms can be assigned a weight value of 10% or lower. The concept can be similar when applying a predetermined weighting function to the first to n-th time-domain waveforms. In this manner, not only a mathematical average, but also a weighted average can be obtained. As described above, the processing unit 105 can average a plurality of sets of time-domain waveforms obtained based on detection signals provided by the detection unit 102 in respective measurement cycles in which the optical delay unit is driven according to the respective speed patterns.

The averaged data can further processed in processing unit 105 and the result can be presented (step S408) by means of displaying or printing (outputting) in a known manner. For example, to present a frequency spectrum, the averaged data of the time-domain waveform is subjected to a Fourier transform, and the frequency spectrum can be displayed or printed for analysis. To present an image by moving a sample, an image is produced by referring to coordinates at which data is measured. The thus produced image can then be stored, transmitted or displayed as necessary.

Figure 3D:
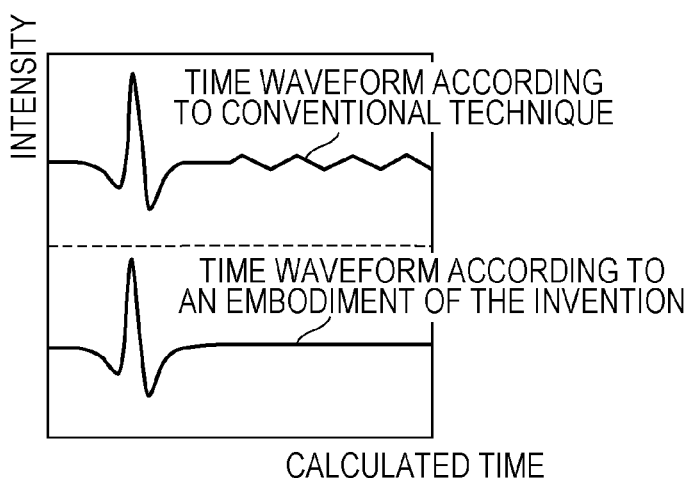
FIG. 3D is a graph provided for explaining a measurement apparatus, a method, and a process according to an embodiment of the present invention.

In the above-described manner, the apparatus and the method according to the present embodiment of the invention enable accurate measurement of the time-domain waveform of the terahertz wave. In the present embodiment, the speed pattern is changed to change the sampling time interval at which to acquire data for use in producing the time-domain waveform of the terahertz wave. The resultant produced time-domain waveform of the terahertz wave does not depend on the sampling time interval, but the change in the sampling time interval results in a change in shape of signal components with low correlation with the terahertz wave. This feature makes it possible to suppress the signal components having low correlation with the terahertz wave by averaging data obtained for various speed patterns. Thus, as shown in FIG. 3D, it is possible to obtain a time-domain waveform in which signal components having less correlation with the terahertz wave are more suppressed than can be achieved by the conventional technique. This makes it possible to suppress a spurious spectrum superimposed on the frequency spectrum and thus it becomes possible to make a measurement for an increased measurement frequency band.

The embodiments of the present invention may also be realized by performing processes as described below. That is, software (a program) for realizing the functions of the embodiment is supplied to a system or an apparatus via a network or a storage medium, and the program is read and executed by a computer (a CPU, a MPU, or the like) in the system or the apparatus. Note that any type of storage medium is usable as long as it is capable of storing the program in a form readable and executable by a computer, so that when the program is executed by the computer, the method of measuring the terahertz wave can be practiced.

Next, a specific example is described below. In the description of the example, similar parts to those described above are not explained again. In the apparatus shown in FIG. 1, the present example of the apparatus is configured as follows. The generating unit 101 and the detection unit 102 are each realized using a photoconductive device including a gallium arsenide film grown at a low temperature and a pattern of an antenna electrode formed on the gallium arsenide film. The laser light source 108 is realized using a titanium-sapphire laser light source configured to output laser light with a pulse width (FWHM) of 50 femtoseconds at a repetition frequency of 80 MHz. The optical delay unit 103 is configured using a one-stage folded optical system and a linear motion stage. A retroreflector is used as the folded optical system. The linear motion stage is configured to be movable over a range of 14 mm (corresponding to an optical path length A needed in acquiring a time-domain waveform). The linear motion stage is driven according to speed patterns managed by the driving speed adjustment unit 104. The driving speed adjustment unit 104 and the processing unit 105 are both realized by a single arithmetic processing unit. In an operation of moving the linear motion stage, the driving speed adjustment unit 104 controls the linear motion stage via a stage driver. The processing unit 105 monitors the output of the current detection unit 107 and the position of the linear motion stage.

The current detection unit 107 includes a current-voltage conversion amplifier and a lowpass filter. In the present example, the conversion ratio of the current-voltage conversion amplifier is set to $1\times10^8$ (V/A). The lowpass filter is configured to have a cutoff frequency of 8 kHz. The bias applying unit 106 is realized using a low-noise DC voltage source. In the present example, the bias applying unit 106 is configured to supply a DC voltage of 30 v to the generating unit 101. In the present example, a time-domain waveform of a terahertz wave is produced without modulating the terahertz wave. For this reason, the time constant τ of the THz-TDS apparatus is given by the time constant of the current detection unit 107. More specifically, the lowpass filter has a time constant of 0.125 msec (the reciprocal of the cutoff frequency), and the time constant τ of the THz-TDS apparatus is given by this time constant of the lowpass filter.

Figure 7:
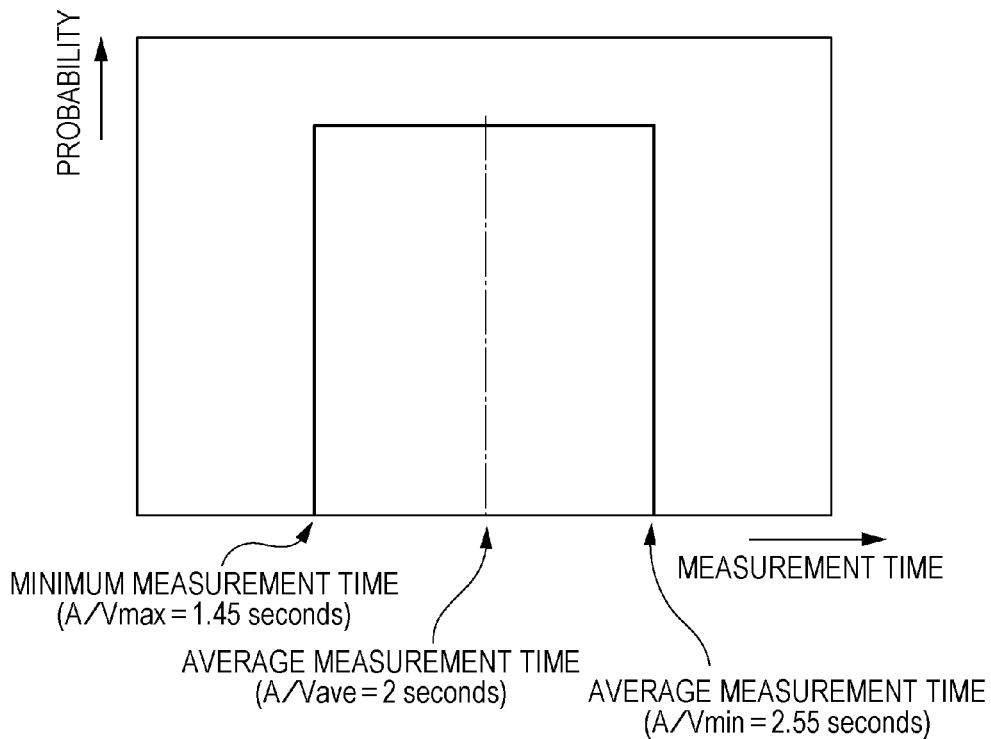
FIG. 7 is a graph illustrating a driving speed included in a speed pattern according to an embodiment of the present invention.

Referring to FIG. 7, the speed pattern used in the present example is described below. In the present example, as shown in FIG. 7, the speed pattern is set such that the probability of occurrence is equal for any value in the range centered at the average measurement time and including values from the minimum measurement time to the maximum measurement time. More specifically, as shown in FIG. 5A, the speed pattern has a speed that changes at a constant speed in each time-domain waveform measurement. In the present example, the number of times the time-domain waveform is measured is set to 100.

The average speed Vave at which the optical delay unit 103 is driven is set to 7 mm/sec. Because the moving range A of the optical delay unit 103 is equal to 14 mm, the average measurement time needed to measure the time-domain waveform of a single terahertz wave is about 2 sec. The time-domain waveform has 4096 measurement points. The optical delay unit 103 moves 3 μm between each adjacent measurement points. Because the optical delay unit 103 employs the folded optical system, the amount of change X in optical path length between each adjacent measurement points is equal to 6 μm/point. As described earlier, X/τ/Vmax is set to be equal to or greater than 5. When parameters are set in the above-described manner, the upper limit of Vmax is 9.6 mm/sec. In the present example, Vmax is set to this value. Note that Vmax may be small than this value depending on a situation. From the values of Vmax and Vave, Vmin is given as 5.5 mm/sec. From these values, in FIG. 7, the average measurement time is 2 sec, the minimum measurement time is about 1.45 sec, and the maximum measurement time is about 2.55 sec. As described above, the speed pattern is selected for each time-domain waveform such that the measurement time falls within the above range.

Figure 8A:
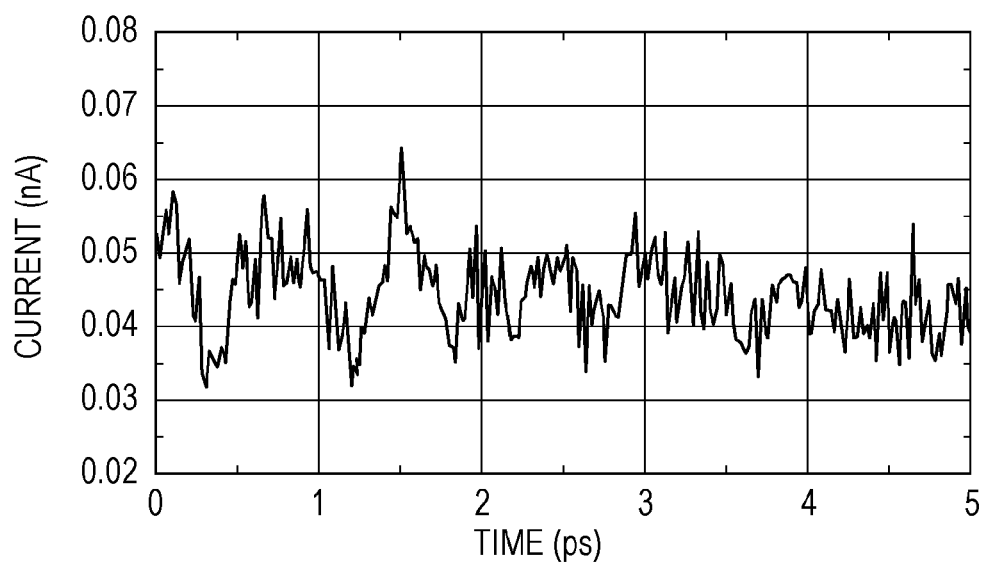
FIG. 8A is a graph illustrating a comparative example of a time-domain waveform.
Figure 8B:
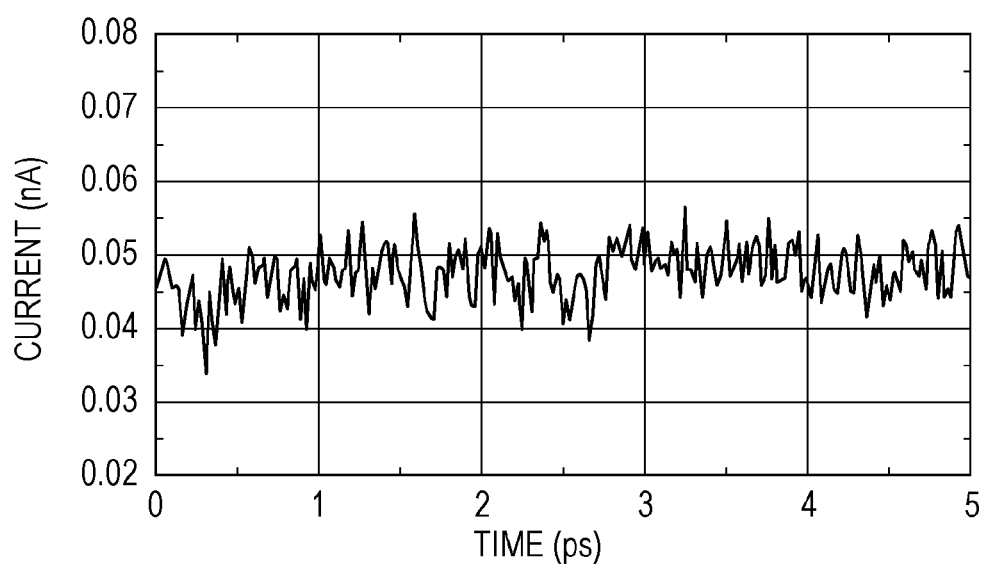
FIG. 8B is a graph illustrating a measured time-domain waveform according to an embodiment of the present invention.

A measurement result using the present example and a comparative measurement result are shown in FIG. 8B and FIG. 8A. Note that in each of FIGS. 8A and 8B, only part of a time-domain waveform of a measured terahertz wave is shown. More specifically, a part immediately before a pulse waveform rises up is extracted from the total time-domain waveform of the terahertz wave and is shown. In these figures, each horizontal axis represents a time axis of the time-domain waveform produced by the processing unit 105. Each vertical axis represents a current output from the detection unit 102 where the value of the current is calculated from the output of the current detection unit 107. FIG. 8A illustrates a comparative measurement result obtained when the optical delay unit 103 is driving according to a fixed speed pattern. More specifically, the linear motion stage of the optical delay unit 103 is driven at a fixed speed equal to Vmax. FIG. 8B illustrates a measurement result obtained in the present example. In the measurement, the speed pattern is randomly selected for each measurement of the time-domain waveform within a range from Vmin to Vmax.

Figure 9A:
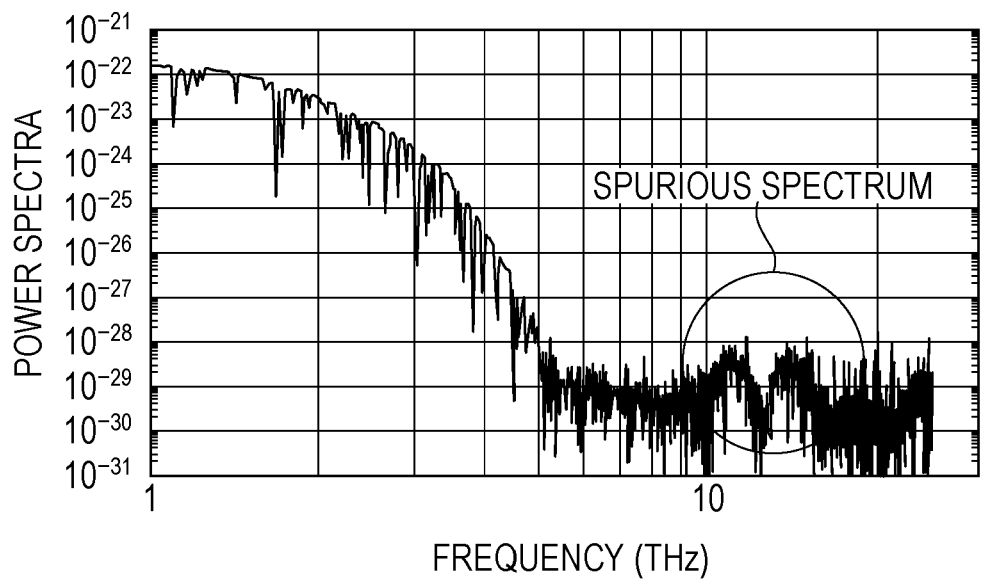
FIG. 9A is a graph illustrating a comparative example of a frequency spectrum.
Figure 9B:
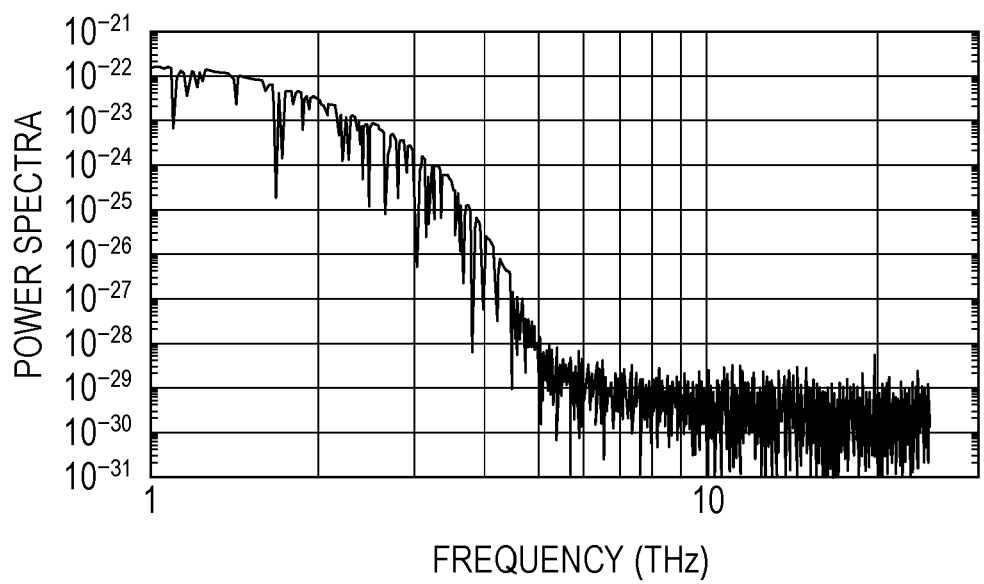
FIG. 9B is a graph illustrating a measured frequency spectrum according to an embodiment of the present invention.

It can be seen from comparison between FIG. 8A and FIG. 8B, there is a difference in the time-domain waveforms obtained. That is, in the time-domain waveform (shown in FIG. 8A) measured using the fixed speed pattern, a signal is detected that has a maximum amplitude of ±0.015 nA and a period of about 1 psec. On the other hand, in the time-domain waveform (shown in FIG. 8B) measured using the speed pattern varied for each measurement, the periodic signal is suppressed. FIGS. 9A and 9B illustrate frequency spectra corresponding to the time-domain waveforms described above. More specifically, FIG. 9A illustrates a frequency spectrum corresponding to the time-domain waveform measured using the fixed speed pattern, and FIG. 9B illustrates a frequency spectrum corresponding to the time-domain waveform measured using the speed pattern varied for each measurement. As can be seen from these two figures, although two spurious spectrum components appear at 10 THz to 11 THz in the spectrum obtained when the fixed speed pattern is used, the spectrum obtained when the speed pattern is changed for each measurement has no spurious spectrum components and has a flat noise floor.

As described above, by changing the speed pattern for each measurement of a time-domain waveform and averaging obtained data, it becomes possible to suppress a signal component having a low correlation with the terahertz wave more effectively than can be by the conventional technique. Thus, it becomes possible to suppress the spurious spectrum superimposed on the frequency spectrum and it becomes possible to increase the measurement bandwidth.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A terahertz time domain spectroscopy apparatus comprising:
    a laser light source;
    a generating unit configured to generate terahertz wave;
    a detection unit configured to detect the terahertz wave;
    an optical system configured to direct laser light from the laser light source to the generating unit or the detection unit;
    a driving unit configured to change an optical path length between the laser light source and the generating unit or the detection unit by moving the optical system;
    a processing unit configured to acquire a time-domain waveform of the terahertz wave based on a detection result of the detection unit,
    wherein the driving unit moves the optical system according to a first speed pattern and a second speed pattern different from the first speed pattern, and
    wherein the processing unit acquires the time-domain waveform based on a first detection result detected by the detection unit in a case where the optical system is moved according to the first speed pattern and a second detection result detected by the detection unit in a case where the optical system is moved according to the second speed pattern.

2. The apparatus according to claim 1, wherein the detection unit acquires the detection result by detecting the terahertz wave from a specimen.

3. The apparatus according to claim 2, wherein the detection unit acquires the first detection result and the second detection result by detecting the terahertz wave from the same specimen.

4. The apparatus according to claim 2, wherein the processing unit acquires information of the specimen based on the time-domain waveform.

5. The apparatus according to claim 2, further comprising:
    a mirror configured to direct the terahertz wave from the generating unit to the specimen; and
    a mirror configured to direct the terahertz wave from the specimen to the detection unit.

6. The apparatus according to claim 1, wherein the driving unit includes a moving part configured to support the optical system and to move, and a driving speed adjustment unit configured to adjust speed of the moving part.

7. The apparatus according to claim 6, wherein the moving part includes a stage.

8. The apparatus according to claim 1, wherein the optical system directs the laser light to the detection unit, and wherein the driving unit changes the optical path length between the laser light source and the detection unit.

* * * * *